United States Patent [19]

Mitterer

[11] Patent Number: 4,791,925

[45] Date of Patent: Dec. 20, 1988

[54] RING REMOVAL TOOL

[76] Inventor: Dennis M. Mitterer, 632 Fourth St., Lancaster, Pa. 17603

[21] Appl. No.: 108,103

[22] Filed: Oct. 13, 1987

[51] Int. Cl.⁴ ............................................. A61B 17/00
[52] U.S. Cl. ................................. 128/303 R; 81/362; 81/420; 81/3.6; 128/334 R
[58] Field of Search ................. 81/420, 424.5, 426.5, 81/417, 302, 427, 300, 442; 128/326, 157, 303 R, 300, 321, 330 R, 345, 17, 20; 29/229, 268; 72/409, 392

[56] References Cited

U.S. PATENT DOCUMENTS

| | | | |
|---|---|---|---|
| 439,994 | 11/1890 | Ballard | 81/302 |
| 514,799 | 2/1894 | Wildt | 81/6 |
| 519,550 | 5/1894 | Riordan | 81/420 |
| 544,268 | 8/1895 | Unsinger | 81/427 |
| 1,178,404 | 4/1916 | Lloyd | 29/223 |
| 1,319,007 | 10/1919 | Kind | 81/302 |
| 1,564,960 | 11/1923 | Horsman | 81/420 |
| 1,810,631 | 6/1931 | Trump | 81/302 |
| 2,607,247 | 8/1952 | Wegs | 81/3.6 |
| 2,887,110 | 5/1959 | Roeschmann | 128/334 R |
| 3,014,610 | 1/1960 | Madeira | 72/409 |
| 3,233,313 | 2/1966 | Roth | 81/302 |
| 3,254,649 | 6/1966 | Wood | 81/302 |
| 4,198,738 | 4/1980 | Wallace | 81/426.5 |

Primary Examiner—Stephen C. Pellegrino
Assistant Examiner—Colleen Reilly
Attorney, Agent, or Firm—Russell J. Egan

[57] ABSTRACT

A ring removal tool has a pair of handles joined by a pivot and biased to a first position by a spring assembly. A pair of head portions on like ends of the handles together from a head with a cylindrical inner surface and a conical outer surface. The tool can be placed about the finger near the ring and the head slipped between the finger and ring. With the ring cut, the tool can exert sufficient force to spread the ring to such size as to enable it to be readily removed from the finger without inflicting harm to the finger.

9 Claims, 2 Drawing Sheets

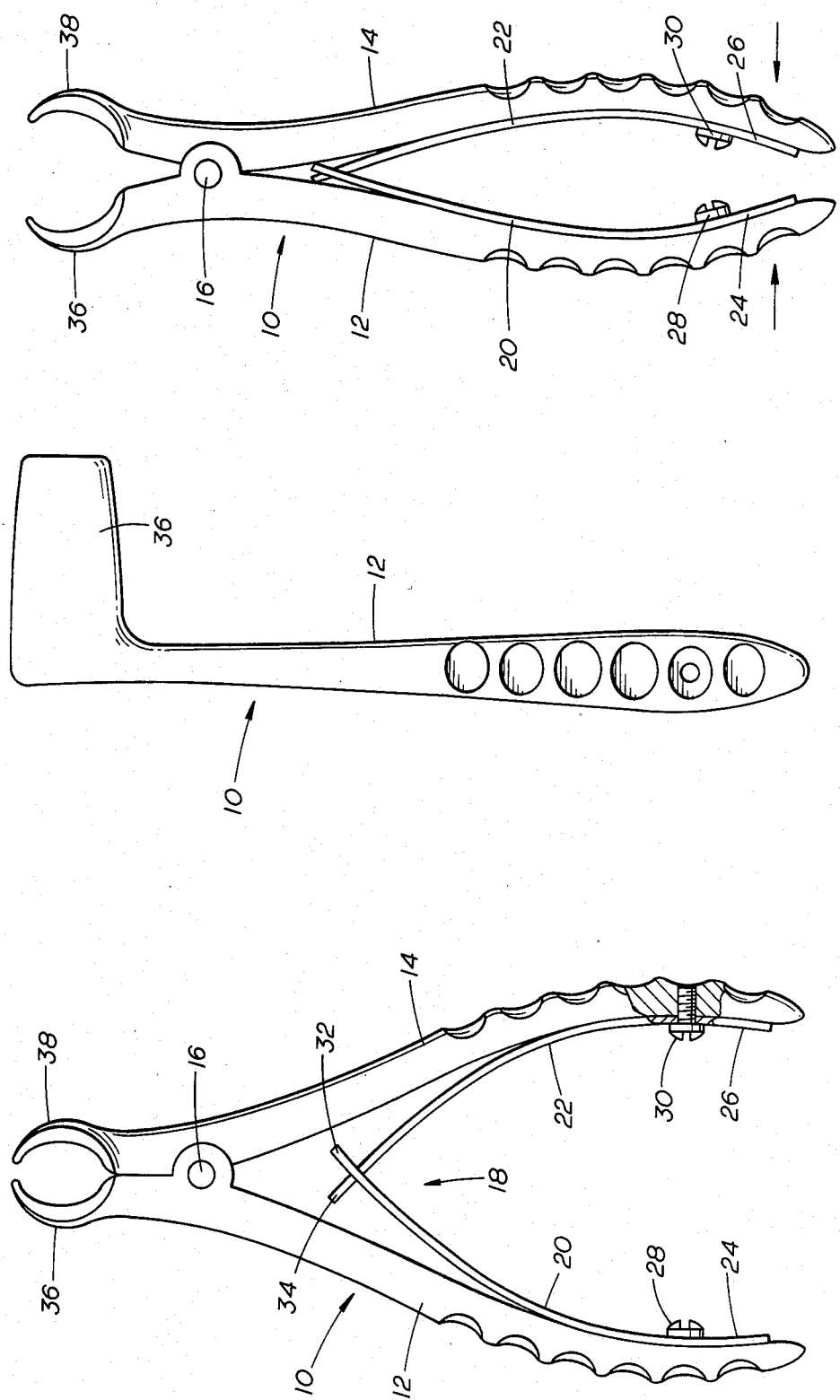

RING REMOVAL TOOL

BACKGROUND OF THE INVENTION

1. The Present Invention

The present invention pertains to a tool for removing rings from fingers and in particular to a tool which spreads the ring and protects the finger as the ring is removed.

2. The Prior Art

Rings are perhaps one of the oldest forms of personal jewelry. They do present problems to the medical field when it becomes necessary to remove a ring from a swollen, lacerated, or otherwise damaged finger without creating additional trauma to the finger. It may be that the ring has become crushed against the finger or that the finger has sustained other damage requiring removal of the ring in order for the finger to be treated. It could also be that the finger has swollen, for any of a number of reasons, and it is now necessary to remove the ring.

Theretofor the rings have been cut by jeweler's saws and then the cut ends spread using available tools, such as needle nose pliers or hemastats. It will be readily appreciated that these tools are awkward to use and can, when they slip, result in further injury to the finger.

There are know devices for spreading bandages and the like for application to a finger. U.S. Pat. No. 2,844,146 is an example. However, these devices do not have the mechanical strength necessary to spread a ring. Known ring spreading tools, such as those shown in U.S. Pat. Nos. 509,226 and 2,887,110, do not have means to protect a finger while moving a ring therealong.

SUMMARY OF THE INVENTION

The present invention is a ring removal tool. The tool has a pair of handles pivotally joined intermediate their ends with a spring, on one side of the pivot, biasing the tool to a first position, and a ring engaging head, on the other side of the pivot, extending a right angles to the handles and formed to be recieved within the ring and to recieve in turn the ring finger therein. The tool is slipped over the finger to lie inside the previously cut ring. When the handles are squeezed together, sufficient pressure is applied to spread the split ring sufficiently to enable it to be removed from the finger without additionally damaging the finger.

The subject tool can have replacable heads to accomodate a wide range of finger sizes or can be produced in a range of sizes to accommodate most fingers. The ring engaging head can have an additional pair of flanges recievable between the cut ends to apply addtional spreading force to the ring when the handles are squeezed together and additional protection for the finger as the ring is removed.

BRIEF DESCRIPTION OF THE DRAWINGS

The present invention will now be described, by way of example, with reference to the accompanying drawings, in which:

FIG. 1 is a plan view of the tool according to the present invention;

FIG. 2 is a side elevation of the tool of FIG. 1;

FIG. 3 is a plan view, similar to FIG. 1, showing the subject tool in an actuated or compressed condition;

DETAILED DESCRIPTION OF THE PREFERRED EMBODIMENT

Figure 4:
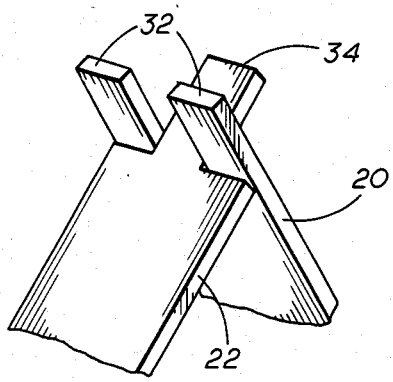
FIG. 4 is a detail of the spring portion of the subject tool.

The preferred embodiment of the subject tool 10 is formed by a pair of handles 12,14 joined by pivot pin 16 intermediate their ends. A spring assembly 18 is fixed between one end of each of the handles biasing them to a first or normally closed condition. This end of each handle has an outwardly directed grip enhancing profile, which can have any of a number of known shapes such as a series of depressions (as shown) or surface knurling. The spring assembly shown is formed by a pair of leaf springs 20,22 each having one end 24,26 secured to a respective end of an adjacent handle by a screw 28,30 and the other ends 32,34 having interdigitated profiles, as best seen in FIG. 4. The other ends of the handles have ring engaging head portions 36,38 extending normal to the plane of the handles. The head portions 36,38 are profiled so that together they form a hollow truncated conical head.

Figure 5:
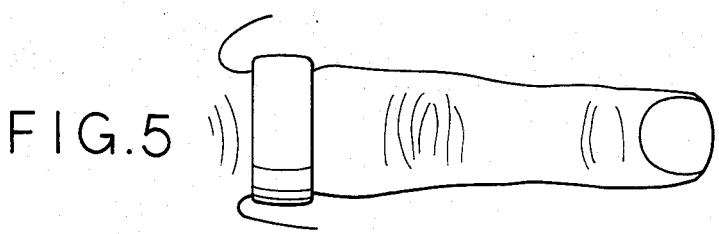
FIGS. 5 to 8 graphic representations of the subject tool in use showing the sequence of removing a ring from a finger.
Figure 6:
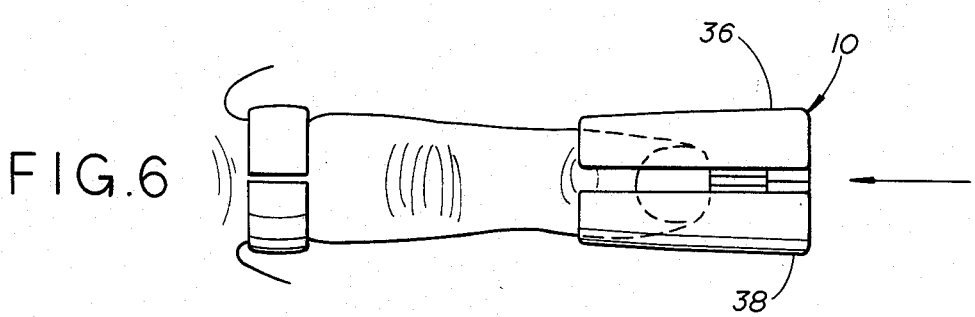
Figure 7:
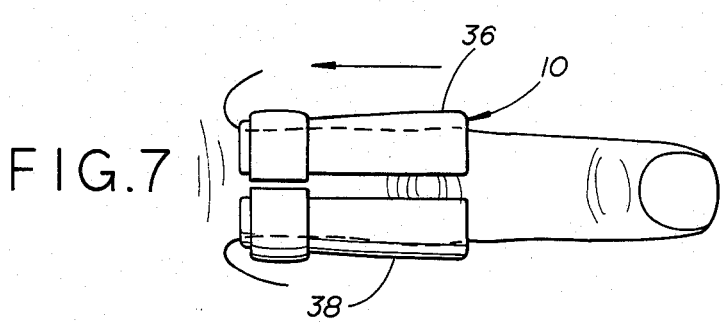
Figure 8:
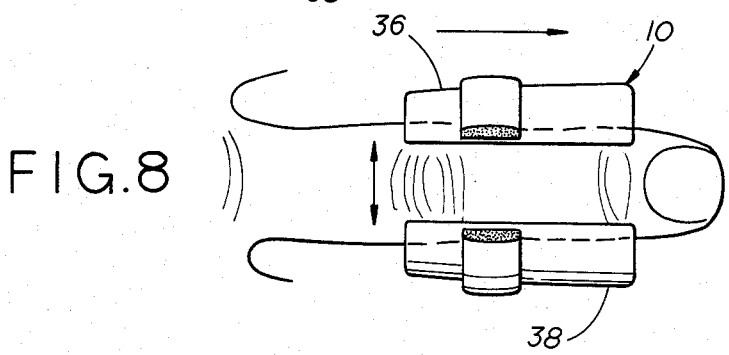

The use of the subject tool is best understood from FIGS. 5 to 8. The finger shown in FIG. 5 is swollen slightly beyond the ring. It would be difficult and/or painful to the patient to remove this ring, especially if there were lacerations etc. present along the finger. The subject tool is placed over the finger (FIG. 6) and moved toward the knuckle until the head portions can be closed and the head slipped between the cut ring and the finger (FIG. 7). The handles are then compressed forcing the cut ends of the ring apart creating adequate ring circumference to allow the easy removal of the ring from the finger. It should be appreciated that during this entire manouver, the tool is always positioned so as to protect the finger from further damage, particularly from the ring.

Figure 9:
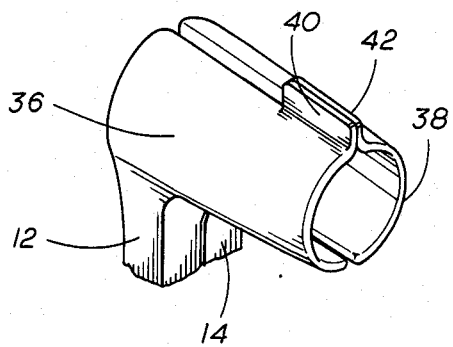
FIG. 9 is a perspective view of an alternate head portion for the subject tool.

An alternate embodiment of the present invention is shown in FIG. 9. In this embodiment a pair of flanges 40,42 extend radially outwardly from one side of the head portions. These flanges would be recieved in between the cut ends of the ring and would both serve to apply pressure to the ring causing it to expand, and to protect the finger by preventing the cut ring ends from inflicting further harm to the finger as the ring is being removed.

Since it is a primary intendion that the subject tool be used in a medical environment, it preferably would be made of stainless steel in order to be steralized by conventional means. However, the tool could also be made of other materials when not medical use is intended, for example by jewelers who must remove rings from fingers grown too large for normal removal of the ring.

It has been found that most rings are made from metals requiring 65–90 psi to spread. A tool with an overall length of 15.5 cm and with the pivot 1.7 cm from the outside edge of the head should be able to adequately produce sufficient force to spread the normal ring. However, the subject tool could be made to accommodate a powered assist, for example and air powered jaw to grip and compress the handles.

The head preferably is made integral with the handles, as shown. In this arrangement there would have to be several tools of different sizes in order to accommodate a variety of finger sizes. Each head portion would be substantially cylindrical inside and have a triuncated conical outer surface enabling it to be moved along the outside of a finger and slide between the ring and the finger. A head having a length of 4 cm should taper from 1.7 cm at the free end to 2 cm at the handle end and would be able to accommodate rings of from size 6 to 9. Similarly, diameters of 1.7 and 1.4 cm should accommodate rings of size 3 to 6. The head portions should preferably be able to spread 2.5 cm without the other ends of the handles touching.

The spring assembly shown is merely representative of any one of a variety to spring configurations which would serve the purposes of the invention. It has been found that the spring assembly shown has certain manufacturing and maintainance advantages. The spring assembly could, in some instances, have the spring located on the same side of the pivot as the head without loosing function of the tool.

While the primary intention of the present invention is the removal of rings from fingers without damaging the finger, there are other functions it could serve. For example, a jeweler could possibly use this tool to reshape a ring which had lost it's circular shape. It could also be used to spread a ring which is to recieve an insert so as to enlarge the ring.

The subject invention may be subject to many modifications and changes without departing from the spirit or essential characteristics of the present invention.

I claim:

1. A ring removal tool comprising:
   a pair of handles pivotally joined intermediate their ends;
   spring means fixed between said handles biasing them to a first closed position; and
   a generally cylindrical ring engaging head integral with and extending normal to a plane defined by said handles, said head being formed by arcuate flanges on like ends of said handles, said head flanges together defining a hollow finger receiving inner cylindrical surface and an outer ring engaging surface tapering away from said handles whereby the tool head can be closed about a finger and moved coaxially therealong to be slipped beneath a cut ring and the handles compressed to exert force to spread the ring sufficiently to allow it to be removed axially along the finger without making further contact therewith.

2. A ring removal tool according to claim 1 wherein said tool is made of medical grade stainless steel.

3. A ring removal tool according to claim 1 wherein said spring means comprises:
   a pair of leaf springs each having one end secured to a respective end of an adjacent handle and the other ends cooperatively interfitting whereby the handles are biased to said first closed condition.

4. A ring removal tool according to claim 1 further comprising a radially outwardly extending flange on each of said head portions adapted to engage the cut ends of the ring to both apply spreading force and protect the finger from the cut ends.

5. A ring removal tool according to claim 1 wherein said spring means and said head are on opposite sides of the pivotal connection of said handles.

6. A ring removal tool according to claim 1 wherein each said handle has a grip enhancing profile.

7. A ring removal tool according to claim 6 wherein said grip enhancing profile is a series of finger gripping depressions.

8. A ring removal tool according to claim 6 wherein said grip enhancing profile is a knurled surface.

9. A method for removing rings from fingers that have swollen or suffered trauma preventing normal removal, said method comprising the steps of:
   cutting the ring at a point along its circumference;
   placing on the finger a ring removal tool having a head with two portions which, when closed, forms substantially a closed cylinder about and protecting the finger;
   moving said tool coaxially along the finger to slide the outer conically tapered surface under the ring;
   applying pressure to the tool to spread said head portions apart causing said ring to spread sufficiently to enable it to be moved coaxially along the finger thereby removing the ring without damage to the finger.

* * * * *